(12) United States Patent
Thompson et al.

(10) Patent No.: US 7,481,795 B2
(45) Date of Patent: Jan. 27, 2009

(54) CIRCUMFERENTIAL TROCAR SEAL ASSEMBLY

(75) Inventors: Brian J. Thompson, Cincinnati, OH (US); Mark S. Zeiner, Mason, OH (US); Paul T. Franer, Cincinnati, OH (US); Michael S. Cropper, Edgewood, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 759 days.

(21) Appl. No.: 11/014,244

(22) Filed: Dec. 17, 2004

(65) Prior Publication Data
US 2006/0135977 A1 Jun. 22, 2006

(51) Int. Cl.
*A61M 5/178* (2006.01)
(52) U.S. Cl. .................................. 604/167.03
(58) Field of Classification Search ..........................
604/167.01–167.04, 264, 164.01–164.12; 606/185
See application file for complete search history.

(56) References Cited

U.S. PATENT DOCUMENTS

| | | | |
|---|---|---|---|
| 3,504,699 A | 4/1970 | Grise | |
| 3,773,233 A | 11/1973 | Souza | |
| 4,436,519 A | 3/1984 | O'Neill | |
| 4,601,710 A | 7/1986 | Moll | |
| 4,610,665 A | 9/1986 | Matsumoto et al. | |
| 4,654,030 A | 3/1987 | Moll | |
| 4,902,280 A | 2/1990 | Lander | |
| 4,931,042 A | 6/1990 | Holmes et al. | |
| 4,932,633 A | 6/1990 | Johnson et al. | |
| 5,030,206 A | 7/1991 | Lander | |
| 5,053,013 A | 10/1991 | Ensminger et al. | |
| 5,104,383 A | 4/1992 | Shichman | |
| 5,203,773 A | 4/1993 | Green | |
| 5,209,737 A | 5/1993 | Ritchart et al. | |
| 5,211,634 A | 5/1993 | Vaillancourt | |
| 5,246,425 A | 9/1993 | Hunsberger et al. | |
| 5,300,033 A | 4/1994 | Miller | |
| 5,308,336 A | 5/1994 | Hart et al. | |
| 5,324,270 A | 6/1994 | Kayan et al. | |
| 5,330,437 A * | 7/1994 | Durman | 604/167.04 |

(Continued)

FOREIGN PATENT DOCUMENTS

EP 0339945 11/1989

(Continued)

*Primary Examiner*—Matthew F Desanto
(74) *Attorney, Agent, or Firm*—Welsh & Flaxman LLC

(57) ABSTRACT

A seal assembly adapted for use in conjunction with a trocar assembly includes a plurality of seal segments. Each seal segment includes a peripheral edge and a seam edge. At least a first seal segment and a second seal segment are connected along their respective peripheral edges to form a first seal layer having a seam defined by the seam edge of the first seal segment and the seam edge of the second seal segment. At least a third seal segment and a fourth seal segment are connected along their respective peripheral edges to form a second seal layer having a seam defined by the seam edge of the third seal segment and the seam edge of the fourth seal segment. The seam of the first seal layer has a first longitudinal axis and the seam of the second seal layer has a second longitudinal axis, and the first seal layer is oriented relative to the second seal layer such that the first longitudinal axis is angularly oriented relative to the second longitudinal axis.

16 Claims, 7 Drawing Sheets

U.S. PATENT DOCUMENTS

| | | | |
|---|---|---|---|
| 5,342,315 A * | 8/1994 | Rowe et al. | 604/167.06 |
| 5,364,372 A | 11/1994 | Danks et al. | |
| 5,366,445 A | 11/1994 | Haber et al. | |
| 5,385,552 A | 1/1995 | Haber et al. | |
| 5,385,553 A | 1/1995 | Hart et al. | |
| 5,441,041 A | 8/1995 | Sauer et al. | |
| 5,456,284 A | 10/1995 | Ryan et al. | |
| 5,467,762 A | 11/1995 | Sauer et al. | |
| 5,534,009 A | 7/1996 | Lander | |
| 5,542,931 A | 8/1996 | Gravener et al. | |
| 5,569,160 A | 10/1996 | Sauer et al. | |
| 5,578,016 A | 11/1996 | Zinger | |
| 5,584,850 A | 12/1996 | Hart et al. | |
| 5,603,702 A | 2/1997 | Smith et al. | |
| 5,643,301 A | 7/1997 | Mollenauer | |
| 5,807,338 A | 9/1998 | Smith et al. | |
| 5,895,377 A | 4/1999 | Smith et al. | |
| 6,024,729 A | 2/2000 | Dehdashtian et al. | |
| 6,086,603 A | 7/2000 | Termin et al. | |
| 6,277,100 B1 | 8/2001 | Raulerson et al. | |
| 6,302,852 B1 | 10/2001 | Fleming, III et al. | |
| 6,352,520 B1 | 3/2002 | Miyazaki | |
| 6,569,120 B1 | 5/2003 | Green et al. | |
| 6,613,063 B1 | 9/2003 | Hunsberger | |
| 6,685,630 B2 | 2/2004 | Sauer et al. | |
| 6,702,787 B2 | 3/2004 | Racenet et al. | |
| 2002/0007153 A1 | 1/2002 | Wells et al. | |
| 2002/0010425 A1 | 1/2002 | Guo et al. | |
| 2004/0049173 A1 | 3/2004 | White et al. | |
| 2004/0064100 A1 | 4/2004 | Smith | |
| 2004/0147949 A1 | 7/2004 | Stellon et al. | |
| 2004/0230161 A1 | 11/2004 | Zeiner | |

FOREIGN PATENT DOCUMENTS

| | | | |
|---|---|---|---|
| EP | 0 567 142 | * | 10/1993 |
| EP | 0567142 | | 10/1993 |
| EP | 0568383 | | 11/1993 |
| EP | 0696459 | | 2/1996 |
| WO | WO 94/03232 | | 2/1994 |
| WO | WO 00/35529 | | 6/2000 |
| WO | WO 2004/033004 | | 4/2004 |

* cited by examiner

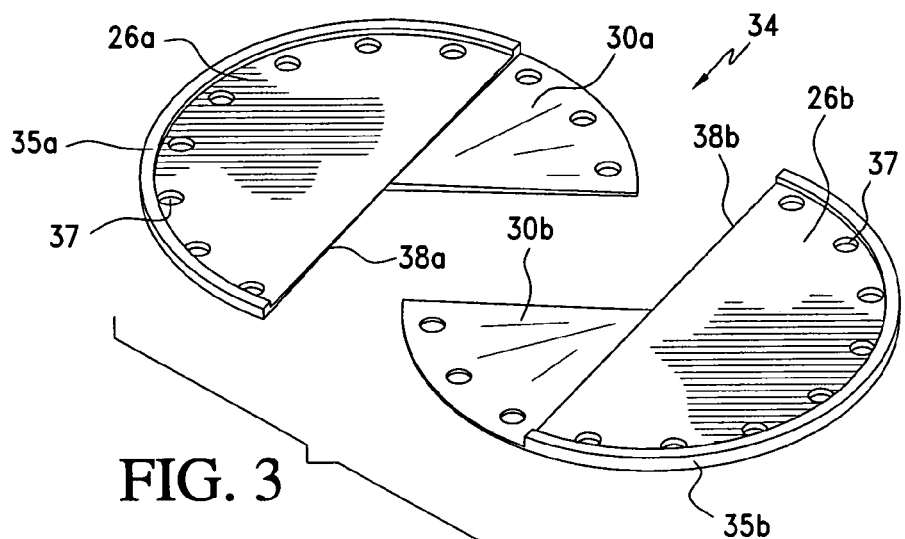
FIG. 3
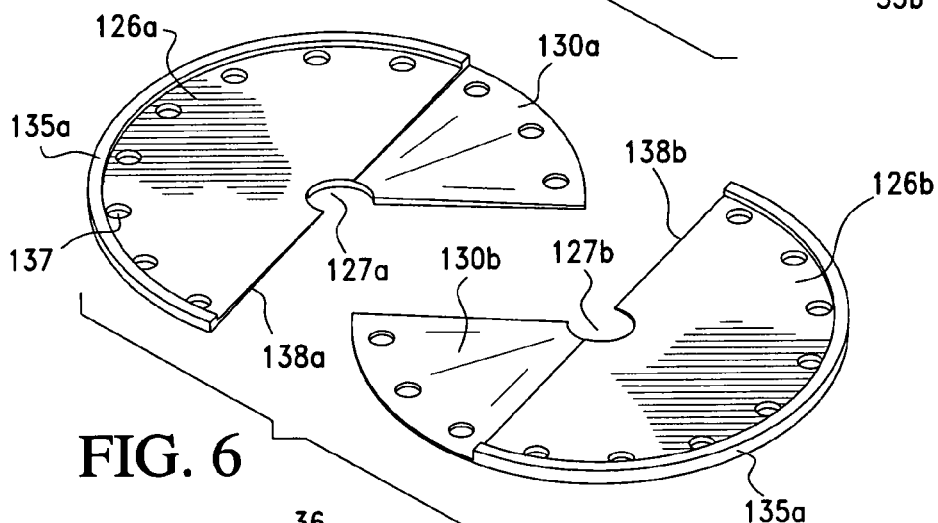
FIG. 6
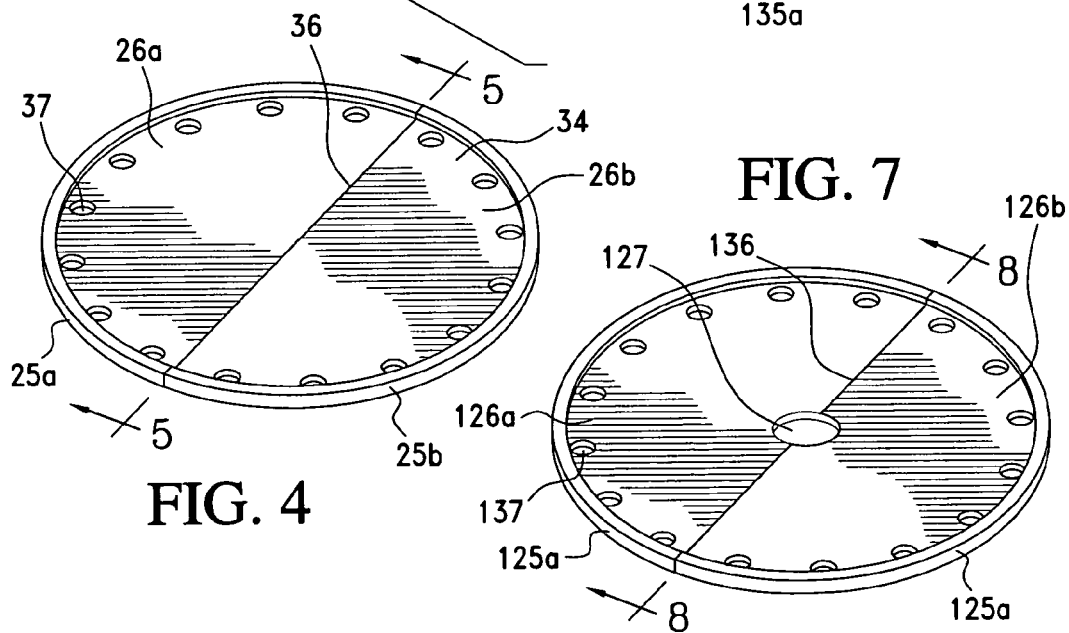
FIG. 4
FIG. 7

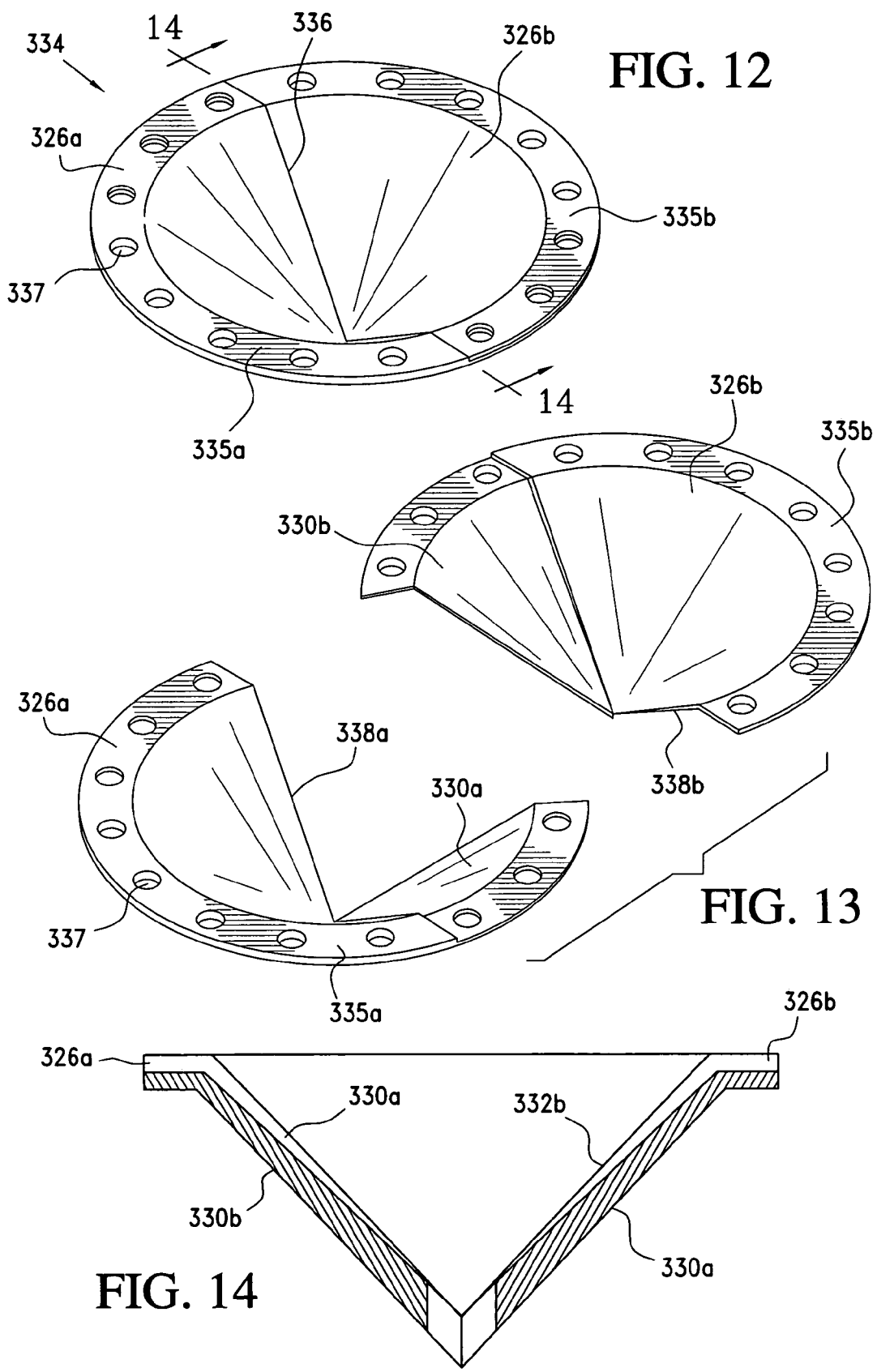

CIRCUMFERENTIAL TROCAR SEAL ASSEMBLY

BACKGROUND OF THE INVENTION

1. Field of the Invention

The invention relates to trocar assemblies. More particularly, the invention relates to a circumferential trocar sealing structure.

2. Description of the Prior Art

A trocar assembly is a surgical instrument that is used to gain access to a body cavity. A trocar assembly generally comprises two major components, a trocar sleeve, composed of a trocar housing and a trocar cannula, and a trocar obturator. The trocar cannula, having the trocar obturator inserted therethrough, is directed through the skin to access a body cavity. Once the body cavity is accessed, laparoscopic or arthroscopic surgery and endoscopic procedures may be performed. In order to penetrate the skin, the distal end of the trocar cannula is placed against the skin that has been previously cut with a scalpel and the trocar obturator is used to penetrate the skin and access the body cavity. By applying pressure against the proximal end of the obturator, the sharp point of the obturator is forced through the skin until it enters the body cavity. The trocar cannula is inserted through the perforation made by the trocar obturator and the trocar obturator is withdrawn, leaving the trocar cannula as an access way to the body cavity.

The proximal end portion of the trocar cannula is typically joined to a trocar housing that defines a chamber having an open distal end portion in communication with the interior lumen defined by the trocar cannula. An obturator, or other elongate surgical instruments or tools, axially extend into and are withdrawn from the trocar cannula through the proximal end portion of the chamber defined by the trocar housing.

Current trocar assemblies are commonly designed with a seal mechanism positioned within the chamber of the trocar housing. The sealing mechanisms are commonly a sealing grommet or gasket through which the obturator or other instruments extend. The sealing mechanism seals against the outer surface of the inserted instruments and thereby prevents fluids and insufflation gas from leaving or entering the body cavity through the trocar cannula. It is desired that such seals provide for good tear resistance, resistance to snagging and low friction with respect to insertion of a device such as a rod, shaft or cylinder.

Seal assemblies are designed to maintain a seal before the insertion of an instrument and after the removal of the instrument. As a result, many trocar assemblies provide double sealing systems. That is, a top, or proximal, seal is used to seal around the tool/instrument when present and a flapper door or duckbill seal is requited below the top seal for sealing the trocar cannula when the instrument is not present.

In contrast, other trocar assemblies employ a single sealing mechanism. Many of these trocar seal assemblies simply employ a silicone seal with a small hole slightly smaller than the smallest tool/instrument to be used in conjunction with the trocar assembly. This type of seal is often referred to as a lip seal. Surgical instruments of various diameters are passed through the lip seal. As such, these seals are often required to provide a seal for use with a full range of instruments. The opening diameter of the seals is, therefore, small relative the largest diameter instruments.

In fact, it is not uncommon for lip seals to be pushed to 400% strain. By forcing these large diameter instruments through a relatively small diameter lip seal, these large diameter instruments are subjected to a significant increase in the normal force upon the instrument shaft. The surgeon feels this increased force as increased drag or resistance to instrument insertion/movement. It is also required that the material properties of the seal be such that the seal does not rip or tear as the seal is stretched to its limit. As a result, a need currently exists for an improved trocar seal assembly overcoming the deficiencies of the prior art.

The present invention overcomes these deficiencies by providing a seal assembly which eliminates the hoop/high stress issues associated with prior art seals and provides a seal assembly which may be utilized either as a single sealing method (reducing the overall complexity of the trocar) or as a proximal seal assembly in a multiseal system.

SUMMARY OF THE INVENTION

It is, therefore, an object of the present invention to provide a seal assembly adapted for use in conjunction with a trocar assembly. The seal assembly includes a plurality of seal segments. Each seal segment includes a peripheral edge and a seam edge. At least a first seal segment and a second seal segment are connected along their respective peripheral edges to form a first seal layer having a seam defined by the seam edge of the first seal segment and the seam edge of the second seal segment. At least a third seal segment and a fourth seal segment are connected along their respective peripheral edges to form a second seal layer having a seam defined by the seam edge of the third seal segment and the seam edge of the fourth seal segment. The seam of the first seal layer has a first longitudinal axis and the seam of the second seal layer has a second longitudinal axis, and the first seal layer is oriented relative to the second seal layer such that the first longitudinal axis is angularly oriented relative to the second longitudinal axis.

It is also an object of the present invention a trocar assembly including a trocar cannula having a proximal end and distal end. The trocar assembly further includes a trocar housing coupled to the proximal end of the trocar cannula for receiving and guiding an obturator through the trocar cannula. The trocar housing includes an open proximal end portion defining an opening provided with a seal assembly. The seal assembly is constructed as described Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 3 is an exploded perspective view of first and second seal segments in accordance with the present invention.

FIG. 4 is a perspective view of a seal layer composed of the first and second seal segments shown in FIG. 3.

FIG. 6 is an exploded perspective view of a further embodiment of first and second seal segments.

FIG. 7 is a perspective view of a seal layer composed of the first and second seal segments shown in FIG. 6.

FIG. 12 is perspective view of a seal layer in accordance with a further embodiment.

FIG. 13 is an exploded perspective view of the first and second seal segments shown in accordance with FIG. 12.

FIG. 14 is a cross sectional view of the seal layer along the line 14-14 of FIG. 12.

DESCRIPTION OF THE PREFERRED EMBODIMENTS

Figure 1:
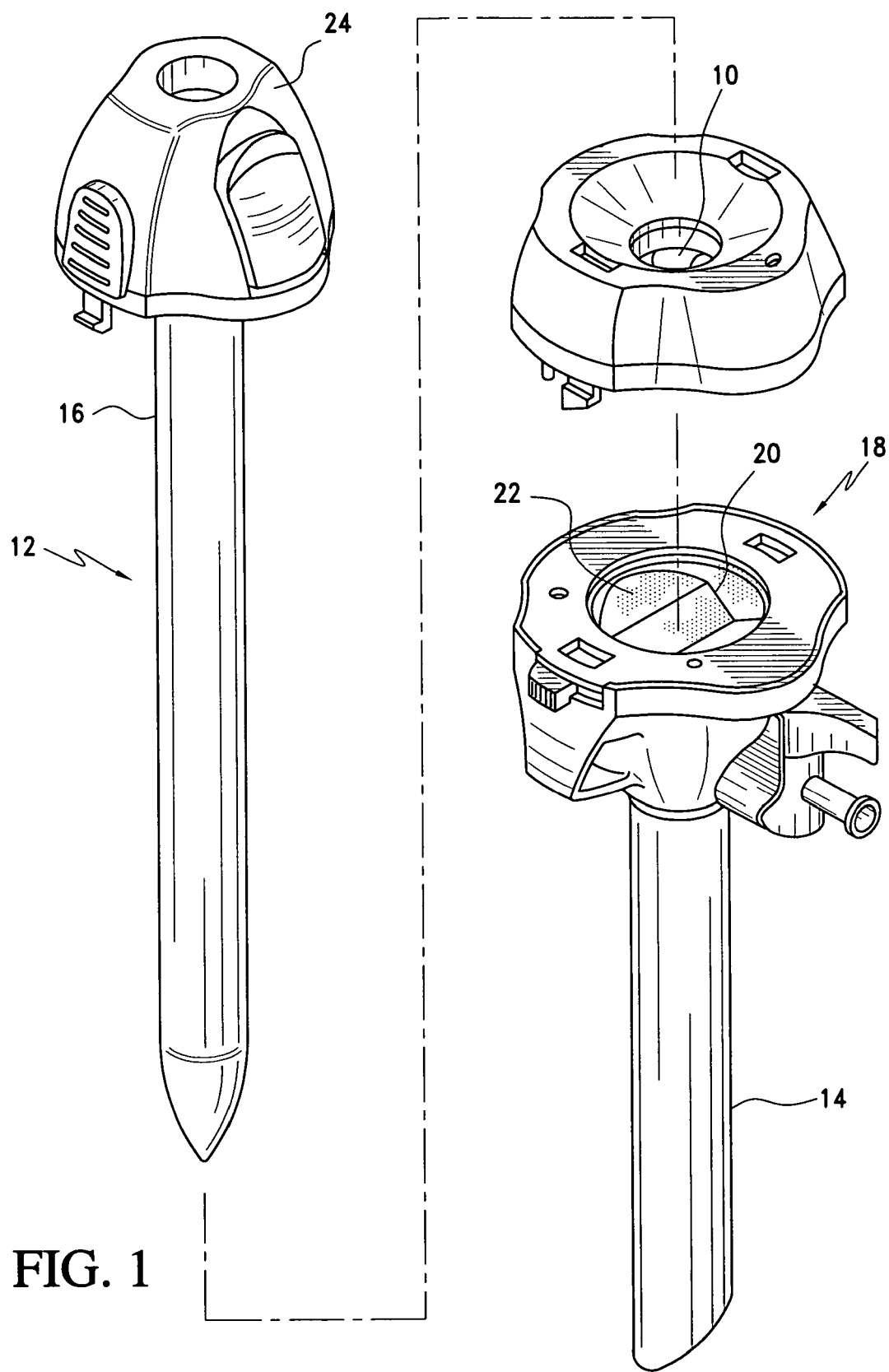
FIG. 1 is an exploded view of a trocar assembly in accordance with the present invention.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1, 2, 3, 4 and 5, a seal assembly 10 for a trocar assembly 12 is disclosed. The seal assembly 10 provides for improved resistance to tearing by reducing the likelihood for tenting to occur. As those skilled in the art will appreciate, tenting occurs when a seal is stretched and thinned out, for example, by an instrument passing through the seal, thus providing an area of weakness which may be easily punctured. As those skilled in the art will certainly appreciate, the present seal assembly 10 is adapted for use with a variety of trocar assemblies 10.

Apart from the seal assembly 10 in accordance with the present invention, the general structure of trocar assembly 12 does not form part of the present invention. For example, and by way of explaining the present seal assembly 10, the trocar assembly 12 may take a variety of forms without departing from the spirit of the present invention.

With that in mind, and by way of example, the trocar assembly 12 includes a trocar cannula 14, a trocar obturator 16 and a trocar housing 18. The trocar cannula 14 defines an interior lumen having an open distal end portion and an open proximal end portion. The proximal end portion extends into and is mounted in the distal end portion of trocar housing 18. The trocar housing 18 has an open proximal end portion that defines an opening 20. The opening 20 is provided with a proximal seal assembly 10 constructed in accordance with the present invention and described in detail hereinbelow. The opening 20 is further provided with a duckbill seal assembly 22 positioned beneath the proximal seal assembly 10. While the present seal assembly 10 is disclosed as a proximal seal assembly 10 forming part of a dual sealing system, the present seal assembly may be utilized in a single seal system without departing from the spirit of the present invention.

The trocar obturator 16 is slidably and removably extendable within the trocar cannula 14 and is inserted into the trocar housing 18 and the trocar cannula 14 through the proximal seal assembly 10, the duckbill seal assembly 22 and the opening 20 of the trocar housing 18. An obturator handle 24 is provided at the proximal end of the trocar obturator 16 and a sharpened point or blade (not shown) is formed at the distal end thereof. As is well known in the art, the seal assembly 10 cooperates with the trocar obturator 16, or another surgical instrument extending through the trocar cannula 14, to sealingly engage the outer surface thereof and thereby preclude the passage of fluids through the trocar housing 18.

With reference to the various embodiments in accordance with the present invention, the proximal seal assembly 10 is composed of multiple overlapping seal segments 26a, 26b, 26a', 26b' assembled so as to minimize leakage between the seal assembly 10 and the insertable rod, shaft or collar of various instruments. In particular, four seal segments 26a, 26b, 26a', 26b' are arranged to create the seal body 28 of the seal assembly 10. While four seal segments are utilized in accordance with a preferred embodiment of the present invention, the seal assembly may ultimately be formed with different numbers of seal segments without departing from the spirit of the present invention.

Figure 2:
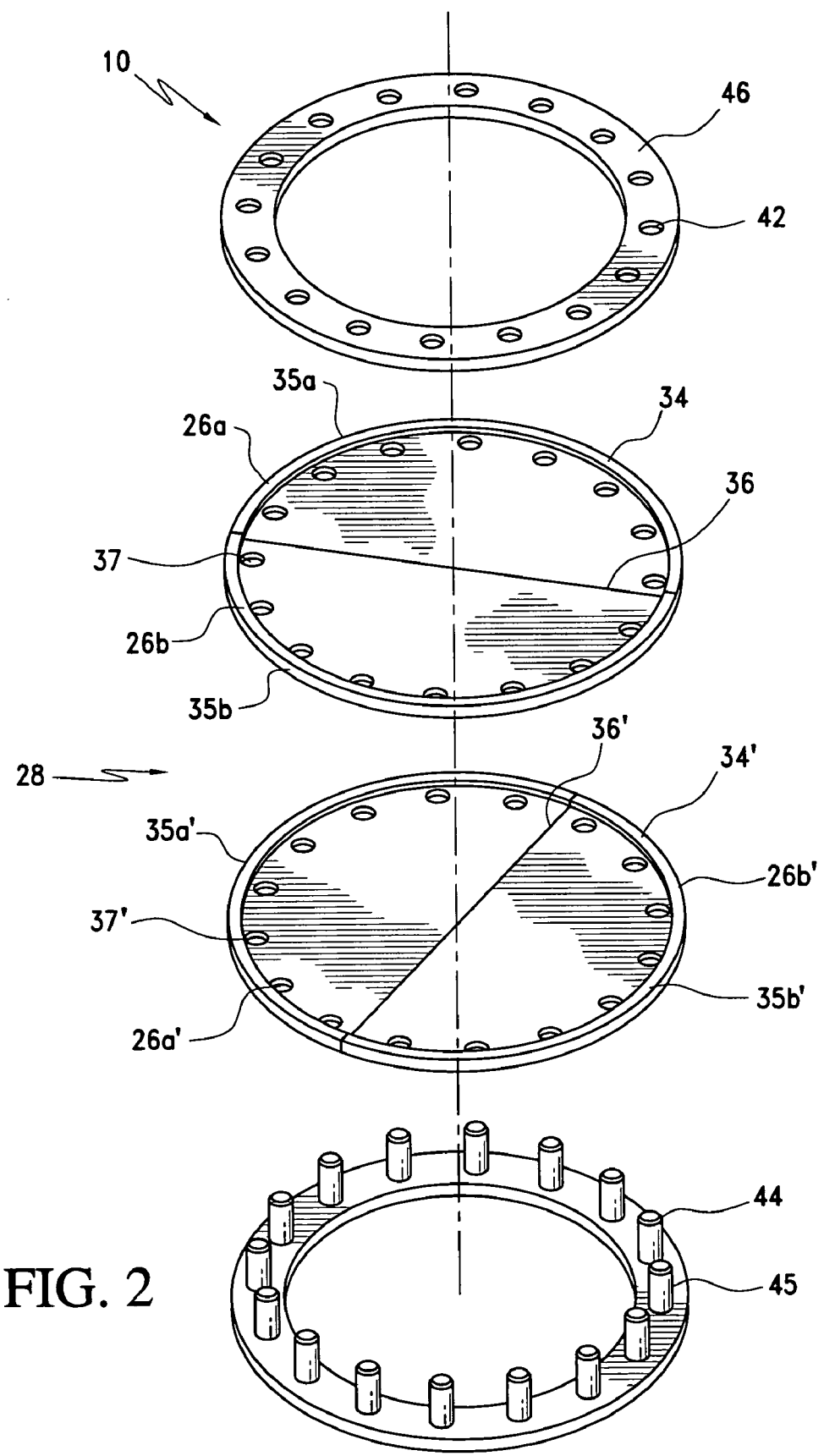
FIG. 2 is an exploded view of the seal assembly in accordance with the embodiment disclosed in FIGS. 3, 4 and 5.

With reference to FIG. 2, a preferred embodiment of the present seal assembly 10 is disclosed. The seal assembly 10 employs several radial seal segments 26a, 26b, 26a', 26b' that fold around the shaft of an inserted instrument. In accordance with the proposed embodiment, hoop stress is eliminated by replacing the single hole of a prior art lip seal with multiple circumferentially positioned seal segments 26a, 26b, 26a', 26b'. These seal segments 26a, 26b, 26a', 26b', when opened with a round probe, provide sealing similar to that provided by the round hole of a prior art lip seal. The present design also utilizes an angled edge feature for wrapping around an instrument shaft while yielding a design that is both easier to mold and inspect.

As will be discussed below in greater detail, the present seal assembly 10 uses a series of interlocking seal segments 26a, 26b, 26a', 26b'. The preferred embodiment disclosed herein employs four seal segments 26a, 26b, 26a', 26b', although more than four seal segments may be utilized without departing from the spirit of the present invention. All four seal segments 26a, 26b, 26a', 26b' are molded individually and then assembled into the final configuration.

The hoop stress of the present seal assembly 10 is reduced by providing a single seal assembly 10 with multiple layers, that is, seal segments 26a, 26b, 26a', 26b', lapped over each other in a manner creating a through hole. The layers form contact zones with the inserted probe. The sum of the contact zones provides contact around the full diameter of the inserted instrument. Without a probe inserted, the seal segments 26a, 26b, 26a', 26b' remain in contact with each other so that the seal assembly 10 allows for no air passage.

The proximal seal assembly 10 is composed of a seal body 28 constructed from two seal layers 34, 34' respectively composed of a pair of seal segments 26a, 26b, 26a', 26b'. Once the two seal layers 34, 34' are properly constructed, the second seal layer 34' is placed beneath the first seal layer 34 with the seal seam 36' of the second seal layer 34' rotated 90° from the seal seam 36 of the first seal layer 34. In this way, the seal seams 36, 36' of the first and second seal layers 34, 34' create a double seamed seal providing for improved circumferential sealing within the trocar housing 18.

Apertures 37, 37' are formed along a peripheral edges 35a, 35b, 35a', 35b' of the respective seal segments 26a, 26b, 26a', 26b' and are spaced such that the apertures 37, 37' will align when the seal layers 34, 34' are properly aligned and rotated 90 degrees. As such, a male retaining ring 44 and a female retaining ring 46 are positioned on opposite sides of the juxtaposed first and second seal layers 34, 34'. The male retaining ring 44 includes a series of connecting prongs 45 that extend through the apertures 37, 37' of the seal layers 34, 34' and are connected with the female openings 47 formed in the female sealing ring 46. In this way, the seal body 28 composed of the first and second seal layers 34, 34' is securely positioned between the male and female retaining rings 44, 46, and ultimately supported for attachment to the trocar housing 18.

Figure 8:
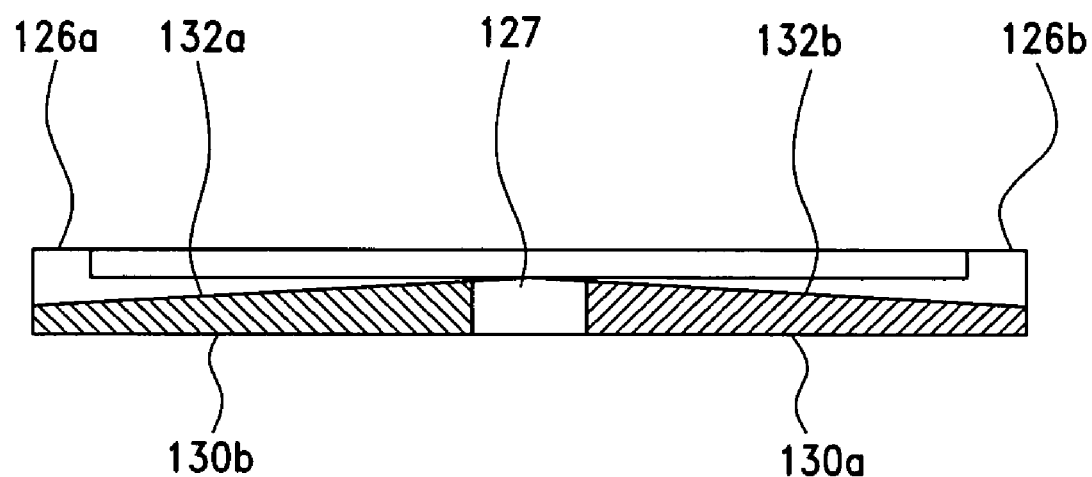
FIG. 8 is a cross sectional view of the seal layer shown in accordance with FIG. 7.

FIG. 2 illustrates an embodiment wherein a seal assembly 10 is provided with seal layers 34, 34' comprising seal segments 26a, 26b, 26a', 26b'. In accordance with this embodiment, the seal segments 26a, 26b, 26a', 26b' leaves no center hole. It is believed this arrangement provides for the best sealing prior to insertion and after removal of the rod. However, and in accordance with an alternate embodiment, an optional clearance opening 127, such as shown in FIGS. 6, 7 and 8, may be utilized.

In practice, when a device such as rod or shaft is inserted through the seal assembly 10, the overlapping segments of the first and second seal layers 34, 34' deflect both downward and around the device inserted. This deflection creates a cat-eye effect on the first seal layer 34, leaving gaps between the inserted device and the first and second seal segments 26a, 26b making up the first seal layer 34. The second seal layer 34', with its seam 36' rotated 90° from the seam 36' of the first seal layer 34', counters the gaps between the inserted device and the seal segments 26a, 26b of first seal layer 34, creating a circumferential seal around the inserted device.

As will be described below in substantial detail, various embodiments in accordance with the present invention are contemplated. The various embodiments describe the application of the concept underlying the present invention to flat seal segments with straight seam edges, flat seal segments with sigmoidal seam edges, cone shaped seal segments with straight seam edges and cone shaped seal segments with sigmoidal seam edges.

While the present seal assembly 10 is specifically adapted for use in conjunction with trocar assemblies, it will be appreciated by those skilled in the art that the present seal assembly may be employed for different functions without departing from the spirit of the present invention.

Figure 5:
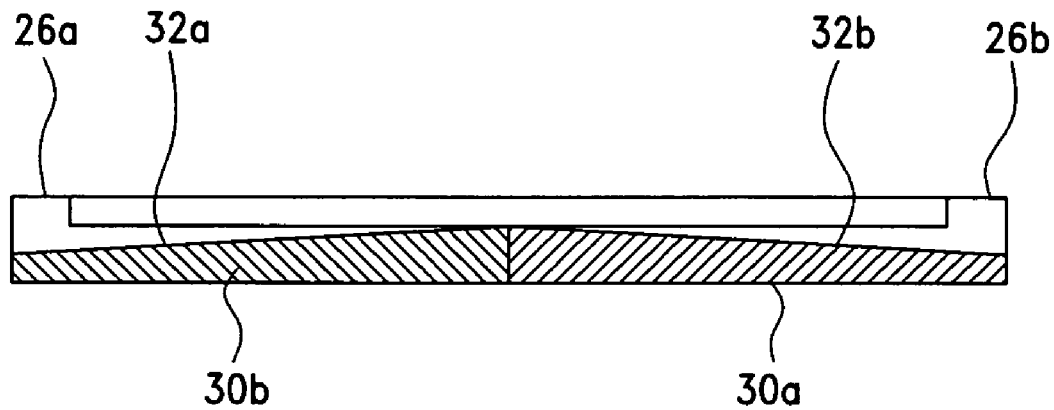
FIG. 5 is a cross sectional view of the seal layer shown in accordance with FIG. 4.

With reference to FIGS. 3, 4 and 5, a preferred embodiment of the seal layer 34 is disclosed. This is the same seal layer 34 disclosed with reference to FIG. 2. Each of the seal segments 26a, 26b in accordance with this embodiment are semi-circular and flat with straight seam edges 38a, 38b. As is shown in FIG. 3, and as described below in greater detail, the use of straight seam edge 38a, 38b produces a seal seam 36 that follows along a substantially straight line.

Referring to FIGS. 3, 4 and 5, each of these flat seal segments 26a, 26b includes a substantially flat semicircular disk having a substantially round peripheral edge 35a, 35b and a straight seam edge 38a, 38b, which defines the straight seal seam 36. In accordance with a preferred embodiment of the present invention, the outer peripheral edge 35a, 35b of each seal segment 26a, 26b defines an arc of approximately 200-220 degrees. The outer peripheral edges 35a, 35b further include a series of apertures 37 that function as a means of attachment for the seal segments 26a, 26b. The seal segments 26a, 26b further include respective tapered angled sections 30a, 30b extending radially for connecting adjacent seal segments 26a, 26b. The angled sections 30a, 30b are respectively tapered on one side. A matching taper 32a, 32b is also formed along the underside of each seal segment 26a, 26b opposite the angled section 30a, 30b. The angled sections 30a, 30b of the seal segments 26a, 26b allow for increased contact between assembled seal segments.

As mentioned above, the radially extending angled sections 30a, 30b are tapered as they extend toward the tip thereof. The underside of each seal segment 26a, 26b opposite the angled section 30a, 30b is similarly formed with a matching taper 32a, 32b to that of the angled section 30a, 30b. In this way, the angled section 30a of the first seal segment 26a is seated within the matching taper 32b along the underside of the second seal segment 26b and the angled section 30b of the second seal segment 26b is seated within the matching taper 32b along the underside of the first seal segment 26a. The matching tapers 32a, 32b permit the formation of a first seal layer 34 including no undesirable ridges or bumps along its underside due to the coupling of the first seal segment 26a to the second seal segment 26b.

In practice, and with reference to FIGS. 3, 4 and 5, two seal segments 26a, 26b are connected in an overlapping relationship to create a first seal layer 34. As such, the resulting first seal layer 34 defines a complete circular outer periphery with a straight seal seam 36 extending between the first and second seal segments 26a, 26b. As will be discussed below, the shape of the seam edges 38a, 38b of the seal segments 26a, 26b ultimately defines the shape of the seal seam 36 extending between the first and second seal segments 26a, 26b making up the first seal layer 34.

As was mentioned above, the concepts underlying the present invention may be practiced through the utilization of a variety of seal layer constructions without departing from the spirit of the present invention. Some of these contemplated constructions are disclosed below. Since it is believe those skilled in the art will appreciate the seal layer will be assembled in a manner similar to that described above with reference to FIG. 2, the details of constructing the complete seal assembly are not be repeated and the following disclosure focuses upon the construction of the individual seal layers.

With reference to FIGS. 6, 7 and 8, a further embodiment in accordance with the present invention is disclosed. This embodiment is substantially similar to that disclosed with reference to FIGS. 3, 4 and 5, but includes a central clearance opening 127. Each of the seal segments 126a, 126b in accordance with this embodiment is semicircular and flat with straight seam edges 138a, 138b. As is shown in FIG. 7, and as described below in greater detail, the use of a straight seam edge 138a, 138b produces a seal seam 136 that follows along a substantially straight line.

Referring to FIGS. 6, 7 and 8, each of these flat seal segments 126a, 126b includes a substantially flat semicircular disk having a substantially round peripheral edge 135a, 135b and a straight seam edge 138a, 138b which defines the straight seal seam 136. Each seal segment 126a, 126b also includes a center clearance recess 127a, 127b, which ultimately define the center clearance opening 127.

In accordance with a preferred embodiment of the present invention, the outer peripheral edge 135a, 135b of each seal segment 126a, 126b defines an arc of approximately 200-220 degrees. The outer peripheral edges 135a, 135b further include a series of apertures 137 that function as a means of attachment for the seal segments 126a, 126b. The seal segments 126a, 126b further include respective tapered angled sections 130a, 130b extending radially for connecting adjacent seal segments 126a, 126b in the manner discussed above. The angled sections 130a, 130b are respectively tapered on one side. A matching taper 132a, 132b is also formed along the underside of each seal segment 126a, 126b opposite the angled section 130a, 130b. The angled sections 130a, 130b of the seal segments 126a, 126b allow for increased contact between assembled seal segments 126a, 126b.

In practice, and with reference to FIGS. 6, 7 and 8, two seal segments 126a, 126b are connected in an overlapping relationship to create a first seal layer 134. As such, the resulting first seal layer 134 defines a complete circular outer periphery with a straight seal seam 136 extending between the first and second seal segments 126a, 126b. As will be discussed below, the shape of the seam edge 138a, 138b of the seal segments 126a, 126b ultimately defines the shape of the seal seam 136 extending between the first and second seal segments making up the first seal layer 134.

Figure 9:
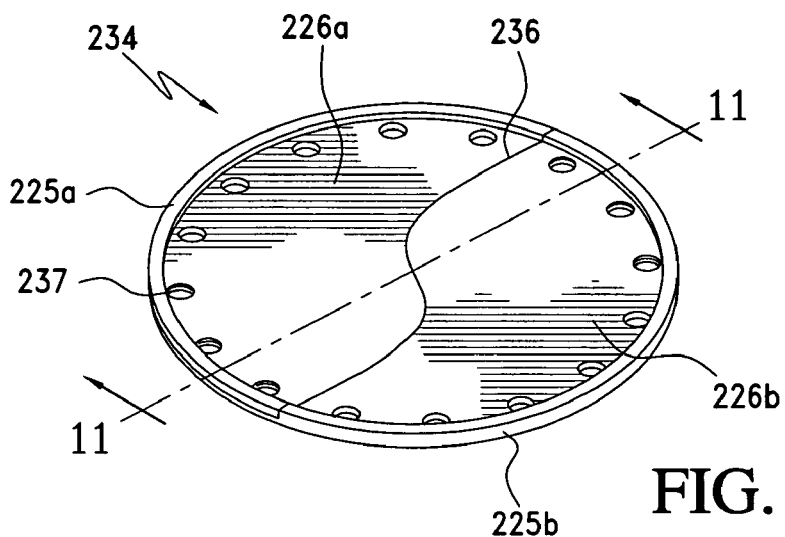
FIG. 9 is a perspective view of an alternate embodiment of a seal layer composed of first and second seal segments in accordance with a further embodiment.
Figure 10:
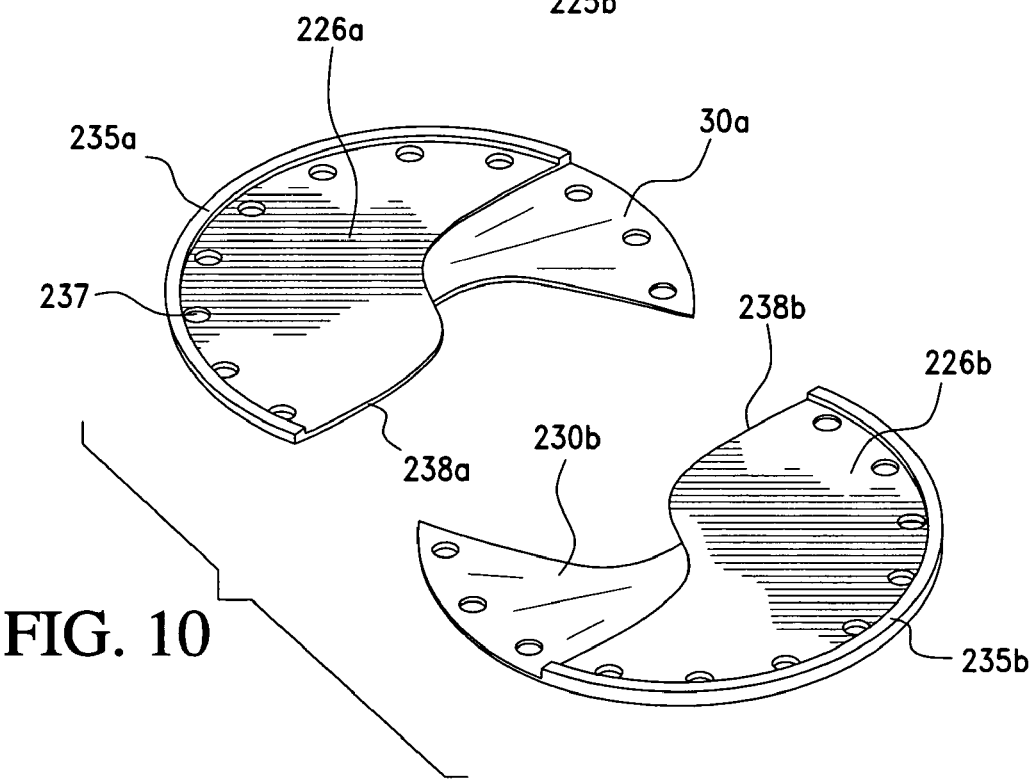
FIG. 10 is an exploded perspective view of the first and second seal segments shown in accordance with FIG. 9.
Figure 11:
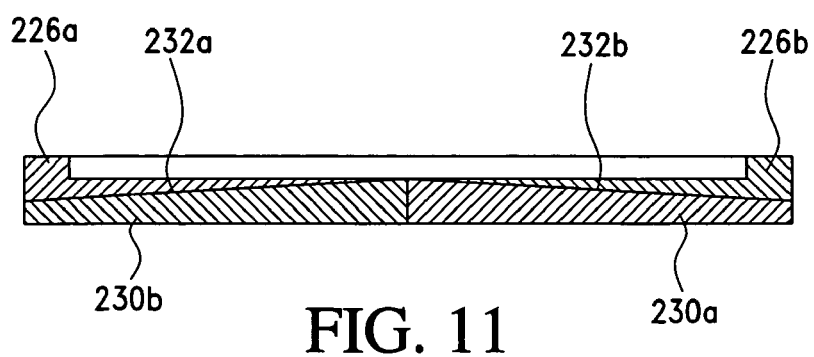
FIG. 11 is a cross sectional view of the seal layer along the line 11-11 of FIG. 9.

A further embodiment is disclosed with reference to FIGS. 9, 10, 11. This embodiment relates to a seal layer 234 composed of flat seal segments 226a, 226b having sigmoidal seam edges 238a, 238b. As is shown in FIG. 10 and is described below in greater detail, the use of sigmoidal seam edges 238a, 238b produces a seal seam 236 that is substantially S-shaped. Each of the flat seal segments 226a, 226b include a substantially flat semicircular disk having a substantially round peripheral edge 235a, 235b and a sigmoidal shaped edge that ultimately defines the seam edge 238a, 238b. Ultimately, a seal body employing two of the present seal layer 224 as described above will create a seal assembly with an S-cut seal seam 236.

In accordance with a preferred embodiment of the present invention, the outer peripheral edges 235a, 235b of each of the seal segments 226a, 226b define an arc of approximately 200-220 degrees. The outer peripheral edges 235a, 235b further include a series of apertures 237 that function as a means of attachment for the seal segments 226a, 226b. The seal segments 226a, 226b further include respective tapered angled sections 230a, 230b extending radially for connecting adjacent seal segments 226a, 226b in the manner discussed above. A matching taper 232a, 232b is also formed along the underside of each of the seal segments 226a, 226b opposite the angled sections 230a, 230b. The angled sections 230a, 230b of the seal segments 226a, 226b allow for increased contact between assembled seal segments 226a, 226b.

In practice, and with reference to the figures, two seal segments 226a, 226b are connected in an overlapping relationship to create a first seal layer 234. As such, the resulting first seal layer 234 defines a complete circular outer periphery with a sigmoidal seal seam 236 extending between the first and second seal segments 226a, 226b. As will be discussed below, the sigmoidal shape of the seam edges 238a, 238b of the respective seal segments 226a, 226b ultimately define the shape of the seal seam 236 extending between the first and second seal segments 226a, 226b making up the first seal layer 234.

Still a further embodiment is disclosed with reference to FIGS. 12, 13 and 14. This embodiment relates to a seal layer 334 composed of cone shaped seal segments 326a, 326b having straight seam edges 338a, 338b. As is shown in the figures and as described below in greater detail, the use of a straight seam edge 338a, 338b produces a seal seam 336 that is substantially straight. The cone shaped seal segments 326a, 326b each include a cone shaped structure that extends about only a portion of a circle. As such, the cone shaped seal segments 326a, 326b may be considered as constituting "a semicircular cone". Each of the semicircular cones includes a flat, substantially round peripheral edge 335a, 335b and a straight seam edge 338a, 338b.

In accordance with a preferred embodiment of the present invention, the outer peripheral edge 335a, 335b of each of the seal segments 326a, 326b defines an arc of approximately 200-220 degrees. The outer peripheral edge 335a, 335b further includes a series of apertures 337 that function as a means of attachment for the seal segments 326a, 326b. The seal segments 326a, 326b further include respective tapered angled sections 330a, 330b extending radially for connecting adjacent seal segments 326a, 326b in the manner discussed above. A matching taper 332a, 332b is also formed along the underside of each of the seal segments 326a, 326b opposite the angled portions 330a, 330b. The angled portions 330a, 330b of the seal segments 326a, 326b allow for increased contact between assembled seal segments 326a, 326b.

In practice, and with reference to the figures, two seal segments 326a, 326b are connected in an overlapping relationship to create a first seal layer 334. As such, the resulting first seal layer 334 defines a complete circular cone with a straight seal seam 336 extending between the first and second seal segments 326a, 326b. As will be discussed below, the shape of the seam edge 338a, 338b of the seal segments 326a, 326b ultimately defines the shape of the seal seam 336 extending between the first and second seal segments 326a, 326b making up the first seal layer 334.

Figure 15:
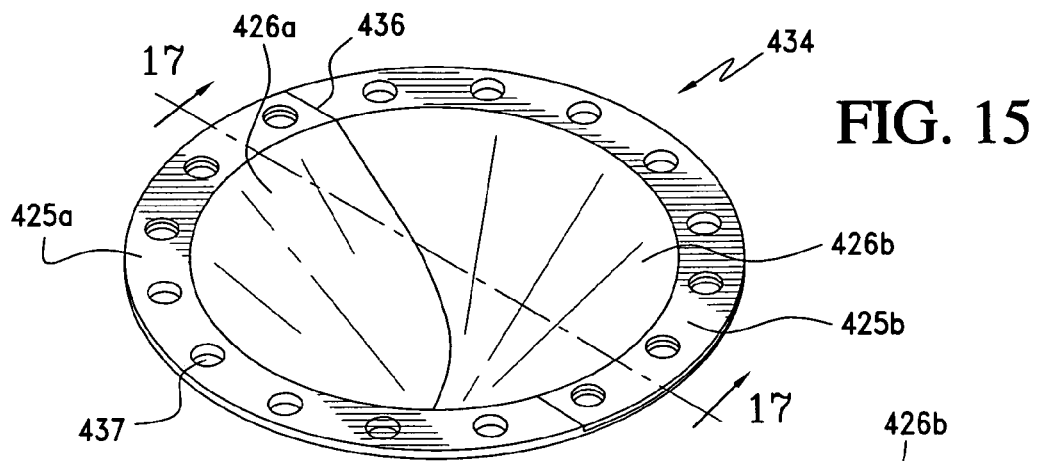
FIG. 15 is a perspective view of a seal layer in accordance with still another embodiment.
Figure 16:
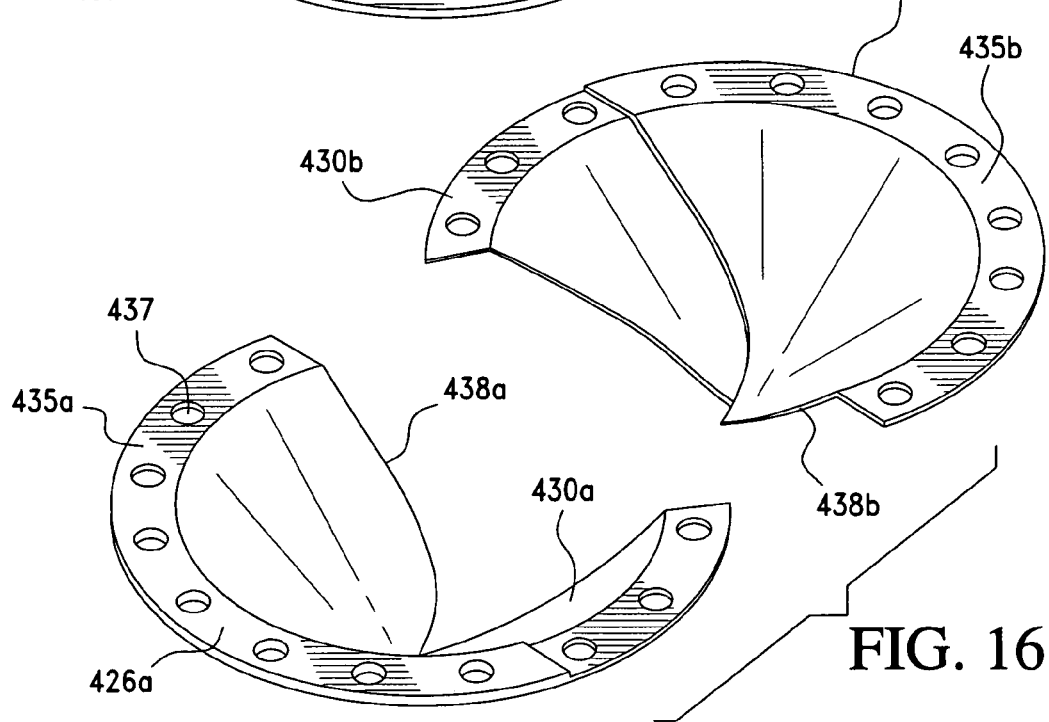
FIG. 16 is an exploded perspective view of the first and second seal segments shown in accordance with FIG. 15.
Figure 17:
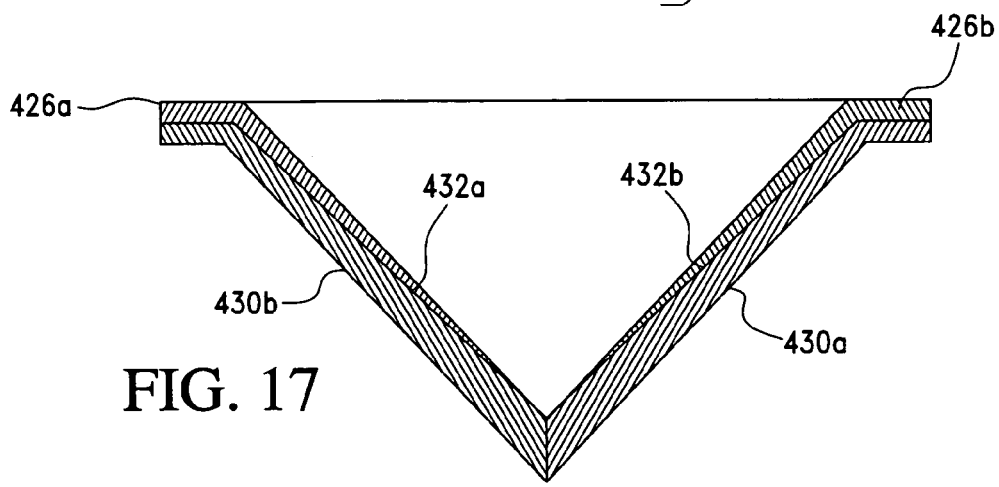
FIG. 17 is a cross sectional view of the seal layer along the line 17-17 of FIG. 15.

Yet a further embodiment is disclosed with reference to FIGS. 15, 16 and 17. This embodiment relates to a seal layer 434 composed of cone shaped seal segments 426a, 426b having sigmoidal seam edges 438a, 438b. The cone feature of this embodiment reduces the potential for seal inversion upon instrument retraction and provides a natural "lead in" towards the center of the coned seal assembly.

As is shown in FIGS. 15, 16 and 17 and as described below in greater detail, a further embodiment of a seal layer 434 composed of seal segments 426a, 426b is disclosed. The use of sigmoidal seam edges 438a, 438b produce a seal seam 436 that is substantially S-shaped. Referring to the figures, each of the cone shaped seal segments 426a, 426b includes a cone shaped structure that extends about only a portion of a circle. As such, the cone shaped seal segments may be consider as constituting "a semicircular cone". The semicircular cone includes a flat, substantially round peripheral edge 435a, 435b and a sigmoidal shaped edge that defines the seam edge 438a, 438b.

In accordance with a preferred embodiment of the present invention, the outer peripheral edges 435a, 435b of the seal segments 426a, 426b define an arc of approximately 200-220 degrees. The outer peripheral edges 435a, 435b further include a series of apertures 437 that function as a means of attachment for the seal segments 426a, 426b. The seal segments 426a, 426b further include tapered angled sections 430a, 430b extending radially for connecting adjacent seal segments 426a, 426b in the manner discussed above. A matching taper 432a, 432b is also formed along the underside of each of the seal segments 426a, 426b opposite the angled sections 430a, 430b. The angled sections 430a, 430b of the seal segments 426a, 426b allow for increase contact between assembled seal segments 426a, 426b.

In practice, two seal segments 426a, 426b are connected along their respective peripheral edges 435a, 435b in an overlapping relationship to create a first seal layer 434. As such, the resulting first seal layer 434 defines a complete circular cone with a seal seam 436 extending between the first and second seal segments 426a, 426b. As will be discussed below, the shape of the seam edge 438a, 438b of the seal segments 426a, 426b ultimately defines the shape of the seal seam 436 extending between the first and second seal segments 426a, 426b making up the first seal layer 434.

The cone feature of the seal assembly reduces the possibility of seal inversion upon instrument retraction. Seal inversion can cause binding of the instrument during retraction creating difficulty when removing instruments from the trocar. The cone feature also provides a natural lead in towards the center of the seal assembly. This guides the instrument inserted towards the center of the seal assembly and reduces the potential of puncturing through the seal at location towards the outer periphery of the cone.

In accordance with a preferred embodiment of the present invention, the seal segments are composed of an elastomer or a cross-linked polymer such as, but not restricted to, silicone or a polyisoprene. However, those skilled in the art will appreciate the possibility that other materials may be employed without departing from the spirit of the present invention.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A seal assembly adapted for use in conjunction with a trocar seal assembly, the seal assembly comprising:
   a plurality of seal segments, each seal segment includes a semi-circular peripheral edge and a seam edge, each seal segment further including an extended angled portion shaped and dimensioned for attachment to an adjacent seal segment, wherein the angled portions are tapered for facilitating coupling of adjacent seal segment;
   at least a first seal segment and a second seal segment are connected along their respective peripheral edges to form a first seal layer having a seam defined by the seam edge of the first seal segment and the seam edge of the second seal segment;
   at least a third seal segment and a fourth seal segment are connected along their respective peripheral edges to form a second seal layer having a seam defined by the seam edge of the third seal segment and the seam edge of the fourth seal segment;
   wherein the peripheral edges of the respective seal segments define an arc of approximately 200-220 degrees; and
   wherein the seam of the first seal layer has a first longitudinal axis and the seam of the second seal layer has a second longitudinal axis, and the first seal layer is oriented relative to the second seal layer such that the first longitudinal axis is angularly oriented relative to the second longitudinal axis.

2. The seal assembly according to claim 1, wherein the first longitudinal axis is oriented approximately 90 degrees relative to the second longitudinal axis.

3. The seal assembly according to claim 1, wherein the seam edges of the respective seal segments are straight.

4. The seal assembly according to claim 1, wherein the seam edges of the respective seal segments are sigmoidal.

5. The seal assembly according to claim 1, wherein the angled portions of the respective seal segments are tapered on one side thereof as they extend toward a tip of the angled portion and a matching taper is formed along the underside of each seal segment for facilitating coupling of adjacent seal segments in the creation of a seal layer.

6. The seal assembly according to claim 1, wherein the first and second seal layers are substantially flat.

7. The seal assembly according to claim 1, wherein the first and second seal layers are substantially cone shaped.

8. The seal assembly according to claim 1, wherein each seal segment is an elastomer of a cross linked polymer.

9. A trocar assembly, comprising:
   a trocar cannula including a proximal end and distal end; and
   a trocar housing coupled to the proximal end of the trocar cannula for receiving and guiding an obturator through the trocar cannula, the trocar housing includes an open proximal end portion defining an opening provided with a seal assembly;
   the seal assembly includes:
   a plurality of seal segments, each seal segment includes a semi-circular peripheral edge and a seam edge, each seal segment further including an extended angled portion shaped and dimensioned for attachment to an adjacent seal segment, wherein the angled portions are tapered for facilitating coupling of adjacent seal segments;
   at least a first seal segment and a second seal segment are connected along their respective peripheral edges to form a first seal layer having a seam defined by the seam edge of the first seal segment and the seam edge of the second seal segment;
   at least a third seal segment and a fourth seal segment are connected along their respective peripheral edges to form a second seal layer having a seam defined by the seam edge of the third seal segment and the seam edge of the fourth seal segment;
   wherein the peripheral edges of the respective seal segments define an arc of approximately 200-220 degrees; and
   wherein the seam of the first seal layer has a first longitudinal axis and the seam of the second seal layer has a second longitudinal axis, and the first seal layer is oriented relative to the second seal layer such that the first longitudinal axis is angularly oriented relative to the second longitudinal axis.

10. The trocar assembly according to claim 9, wherein the first longitudinal axis is oriented 90 degrees relative to the second longitudinal axis.

11. The trocar assembly according to claim 9, wherein the seam edges of the respective seal segments are straight.

12. The trocar assembly according to claim 9, wherein the seam edges of the respective seal segments are sigmoidal.

13. The trocar assembly according to claim 9, wherein the angled portions of the respective seal segments are tapered on one side thereof as they extend toward a tip of the angled portion and a matching taper is formed along the underside of each seal segment for facilitating coupling of adjacent seal segments in the creation of a seal layer.

14. The trocar assembly according to claim 9, wherein the first and second seal layers are substantially flat.

15. The trocar assembly according to claim 9, wherein the first and second seal layers are substantially cone shaped.

16. The seal assembly according to claim 9, wherein each seal segment is an elastomer of a cross linked polymer.

* * * * *